(12) United States Patent
Takenaka et al.

(10) Patent No.: US 6,878,672 B2
(45) Date of Patent: Apr. 12, 2005

(54) HERBICIDAL EMULSION COMPOSITIONS

(75) Inventors: Junji Takenaka, Tokuyama (JP); Kayoko Takagi, Tokuyama (JP); Shozo Kato, Tokuyama (JP)

(73) Assignee: Tokuyama Corporation, Tokuyama (JP)

( * ) Notice: Subject to any disclaimer, the term of this patent is extended or adjusted under 35 U.S.C. 154(b) by 11 days.

(21) Appl. No.: 10/240,106

(22) PCT Filed: Jan. 28, 2002

(86) PCT No.: PCT/JP02/00603

§ 371 (c)(1),
(2), (4) Date: Sep. 27, 2002

(87) PCT Pub. No.: WO02/060253

PCT Pub. Date: Aug. 8, 2002

(65) Prior Publication Data

US 2003/0191024 A1 Oct. 9, 2003

(30) Foreign Application Priority Data

Jan. 29, 2001 (JP) ...................... 2001-019799

(51) Int. Cl.$^7$ .............................. A01N 25/32
(52) U.S. Cl. ...................... 504/105; 504/107
(58) Field of Search ................. 504/105, 107

(56) References Cited

U.S. PATENT DOCUMENTS

| 4,331,468 A | | 5/1982 | Williams ...................... 71/121 |
| 4,622,061 A | * | 11/1986 | Alt .............................. 504/294 |
| 6,083,873 A | * | 7/2000 | Fukada et al. .............. 504/105 |

FOREIGN PATENT DOCUMENTS

| EP | 901752 A1 | 3/1999 |
| JP | 5-15699 B2 | 3/1993 |
| JP | 11-79906 A | 3/1999 |

* cited by examiner

Primary Examiner—S. Mark Clardy
(74) Attorney, Agent, or Firm—Birch, Stewart, Kolasch & Birch, LLP

(57) ABSTRACT

A herbicidal emulsion composition comprising an ethenylamide compound as a herbicidally active component and a dichloroacetamide compound as a phytotoxicity reducing agent. This composition has excellent keeping stability because the phytotoxicity reducing agent of the composition does not decompose and crystals do not separate out even when it is kept for a long time. An amino alcohol and a polar nonaqueous solvent as a solvent are added to the ethenylamide compound and the dichloroacetamide compound to prepare a herbicidal emulsion composition.

20 Claims, No Drawings

HERBICIDAL EMULSION COMPOSITIONS

This application is a national phase under 35 U.S.C. § 371 of PCT International Application No. PCT/JP02/00603 which has an International filing date of Jan. 28, 2002, which designated the United States of America.

FIELD OF THE INVENTION

The present invention relates to a herbicidal emulsion composition which comprises an ethenylamide compound as a herbicidally active component and a dichloroacetamide compound as a phytotoxicity reducing agent.

DESCRIPTION OF THE PRIOR ART

It is known that ethenylamide compounds have excellent herbicidal activity (refer to JP-B 5-15699) (the term "JP-B" as used herein means an "examined Japanese patent publication"). Out of these, an ethenylamide compound having an aryl group or heteroaryl group at the 1-position of an ethenyl group may be used as a herbicide for broad-leaved crops such as soybeans, cotton and beets, and the crops of the grass family such as wheat, barley, corn and upland rice. However, phytotoxicity such as the dead or yellowed leaves of cultivated crops, the suppressed growth of the crops or the reduced yield may occur according to the type of the soil of the crop cultivation land, the amount of water content or temperature.

It is known that a phytotoxicity reducing agent is used as means of reducing such phytotoxicity. It is also known that the above ethenylamide compound is used in conjunction with a phytotoxicity reducing agent such as a dichloroacetamide compound to prevent the occurrence of phytotoxicity (refer to JP-A 11-79906) (the term "JP-A" as used herein means an "unexamined published Japanese patent application").

In general, herbicides are provided as preparations whose effective components including a herbicidally active component can be easily sprinkled in order to simplify the work of a sprinkling person. Out of these, an emulsion which is an uniform liquid comprising effective components, surfactant (may not be contained in an emulsion composition as it may be added to dilute an emulsifier with water) and a solvent is diluted with water to be emulsified before use. Since the production process of the emulsion is simple and the price of the emulsion is low, it is widely used now. Therefore, even a herbicide comprising an ethenylamide compound having excellent herbicidal activity and a dichloroacetamide compound as a phytotoxicity reducing agent is desired to be prepared as an emulsion which contains these two components at the same time.

However, it has been revealed that when an emulsion is prepared by mixing the ethenylamide compound, dichloroacetamide compound and a surfactant with a solvent in accordance with a general method and kept for a long time, its phytotoxicity reducing effect is reduced.

The inventors of the present invention have first investigated the cause of reducing the phytotoxicity reducing effect to solve the above problem. As a result, it has been found that the phytotoxicity reducing effect is reduced by the decomposition of the dichloroacetamide compound as a phytotoxicity reducing agent due to a trace amount of an acidic component as an impurity contained in the ethenylamide compound.

It has also been found that when a basic compound such as an alkylamine is added to form a salt with the acidic component in order to suppress the decomposition of the dichloroacetamide compound, the decomposition of the dichloroacetamide compound can be prevented. However, it has been made clear that the salt causes a new problem that it does not dissolve in the emulsion and forms a nucleus from which the ethenylamide compound or the dichloroacetamide compound is crystallized and when the crystal separates out and the emulsion is diluted with water and sprayed with a sprayer, the sprayer is blocked, thereby making it impossible to carry out a treatment.

SUMMARY OF THE INVENTION

It is an object of the present invention to solve the above problem, that is, provide a herbicidal emulsion composition which comprises an ethenylamide compound as a herbicidally active component and a dichloroacetamide compound as a phytotoxicity reducing agent and has excellent keeping stability without a reduction in its phytotoxicity reducing effect even when it is kept for a long time.

It is another object of the present invention to provide a herbicidal emulsion composition which comprises an amino alcohol as a basic compound and a polar nonaqueous solvent as a solvent to form a salt uniformly soluble in the emulsion without causing the deposition of a crystal through a reaction between the amino alcohol and the acidic component so that the decomposition of a phytotoxicity reducing agent can be prevented.

Other objects and advantages of the present invention will become apparent from the following description.

According to the present invention, the above objects and advantages of the present invention are attained by a herbicidal emulsion composition comprising:

(A) a herbicidally active component which is an ethenylamide compound represented by the following formula (1):

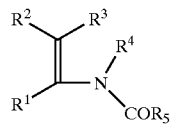

(1)

wherein $R^1$ is a substituted or nonsubstituted heteroaryl group having 3 to 8 carbon atoms and containing 1 to 2 hetero atoms selected from the group consisting of oxygen atom, sulfur atom and nitrogen atom, or substituted or nonsubstituted aryl group having 6 to 14 carbon atoms, $R^2$ and $R^3$ are each independently a hydrogen atom or alkyl group having 1 to 12 carbon atoms and may be bonded together to form a ring with a carbon atom bonded thereto, $R^4$ is a substituted or nonsubstituted alkyl group having 1 to 12 carbon atoms, substituted or nonsubstituted alkenyl group having 2 to 12 carbon atoms, substituted or nonsubstituted alkynyl group having 2 to 12 carbon atoms, substituted or nonsubstituted aryl group having 6 to 14 carbon atoms, substituted or nonsubstituted heteroaryl group having 3 to 8 carbon atoms, substituted or nonsubstituted cycloalkyl group having 3 to 6 carbon atoms, substituted or nonsubstituted cycloalkenyl group having 4 to 6 carbon atoms, or substituted or nonsubstituted heterocycloalkyl group having 4 to 5 carbon atoms, and $R^5$ is a substituted or nonsubstituted heteroaryl group having 3 to 8 carbon atoms and containing 1 to 2 hetero atoms selected from the group consisting of oxygen atom, sulfur atom and nitrogen atom, substituted or nonsubstituted aryl group having 6 to 14 carbon atoms, or substituted or nonsubstituted alkyl group having 1 to 12 carbon atoms, (B) a phytotoxicity reducing agent which is a dichloroacetamide compound represented by the following formula (2):

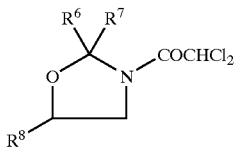
(2)

wherein $R^6$ and $R^7$ are each independently a hydrogen atom or alkyl group having 1 to 3 carbon atoms, and $R^8$ is a hydrogen atom, alkyl group having 1 to 3 carbon atoms, or substituted or nonsubstituted heteroaryl group having 3 to 8 carbon atoms and containing 1 to 2 hetero atoms selected from the group consisting of oxygen atom, sulfur atom and nitrogen atom, or the following formula (3):

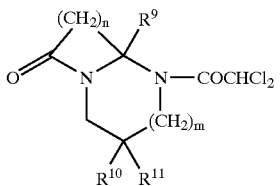
(3)

wherein $R^9$, $R^{10}$ and $R^{11}$ are each independently a hydrogen atom or alkyl group having 1 to 2 carbon atoms, n is 2 or 3, and m is 0 or 1,
(C) an amino alcohol, and
(D) a polar nonaqueous solvent.

BEST MODE FOR CARRYING OUT THE INVENTION

In the herbicidal emulsion composition of the present invention, it is assumed that a desired effect is obtained because the acidic component which is contained in the ethenylamide compound in a slight amount as an impurity and causes the decomposition of the dichloroacetamide compound is reacted with the amino alcohol to form a salt which does not involve in the decomposition of the dichloroacetamide compound and further the salt is completely dissolved in the polar nonaqueous solvent.

When the herbicidal emulsion composition of the present invention comprises an ethenylamide compound of the above formula (1) in which $R^1$ is a substituted or nonsubstituted aryl group having 6 to 14 carbon atoms, $R^2$ and $R^3$ are each independently a hydrogen atom or alkyl group having 1 to 12 carbon atoms, and may be bonded together to form a ring with a carbon atom bonded thereto, $R^4$ is a substituted or nonsubstituted alkyl group having 1 to 12 carbon atoms, and $R^5$ is a substituted or nonsubstituted alkyl group having 1 to 12 carbon atoms, it has high herbicidal activity and can be produced easily because its raw materials can be easily acquired. When the herbicidal emulsion composition comprising a dichloroacetamide compound of the above formula (2) in which $R^6$, $R^7$ and $R^8$ are each independently a hydrogen atom, methyl group or a dichloroacetamide compound of the above formula (3) in which $R^9$, $R^{10}$ and $R^{11}$ are each independently a hydrogen atom or methyl group, it has a high phytotoxicity reducing effect and can be easily produced because its raw materials can be easily acquired. Further, when the above specific ethenylamide compound and the above specific dichloroacetamide compound are used in combination, the obtained composition is particularly preferred because it has the characteristic properties of the both compounds.

EMBODIMENTS OF THE INVENTION

The herbicidal emulsion composition of the present invention comprises an ethenylamide compound represented by the above formula (1) as a herbicidally active component. It is known that the ethenylamide compound represented by the above formula (1) has herbicidal activity (refer to JP-B 5-15699).

A description is subsequently given of the ethenylamide compound represented by the above formula (1).

In the above formula (1), $R^1$ is a substituted or nonsubstituted heteroaryl group having 3 to 8 carbon atoms and containing 1 to 2 hetero atoms selected from the group consisting of oxygen atom, sulfur atom and nitrogen atom, or substituted or nonsubstituted aryl group having 6 to 14 carbon atoms. The number of carbon atoms of each group does not include the number of carbon atoms contained in the substituent of the group (the same shall apply to other groups).

Examples of the above nonsubstituted heteroaryl group include furyl group, thienyl group, pyrrolyl group, pyridyl group, pyrimidinyl group, benzofuryl group, benzothienyl group, indolyl group, quinolyl group, thiazolyl group, pyrazolyl group, oxazolyl group and benzoxazolyl group. Examples of the nonsubstituted aryl group include phenyl group, naphthyl group, anthranyl group and phenanthrenyl group.

The substituted heteroaryl group and substituted aryl group are the above nonsubstituted heteroaryl group and nonsubstituted aryl group having an alkyl group such as methyl group, ethyl group or propyl group; halogen atom such as chlorine atom, bromine atom, iodine atom or fluorine atom; alkoxy group such as methoxy group, ethoxy group or propoxy group; alkylthio group such as methylthio group, ethylthio group or propylthio group; cyano group; nitro group; or amino group as a substituent, respectively. Illustrative examples of the substituted aryl group and substituted heteroaryl group include methylphenyl group, ethylphenyl group, propylphenyl group, butylphenyl group, hexylphenyl group, dimethylphenyl group, methyl(ethyl) phenyl group, ethyl(propyl)phenyl group, chlorophenyl group, bromophenyl group, fluorophenyl group, dichlorophenyl group, methoxyphenyl group, ethoxyphenyl group, propoxyphenyl group, dimethoxyphenyl group, cyanophenyl group, nitrophenyl group, chloro(methyl)phenyl group, methoxy(methyl)phenyl group, methylthiophenyl group, (trifluoromethyl)phenyl group, (amino)dimethylphenyl group, chloro(nitro)phenyl group, methylnaphthyl group, chloronaphthyl group, methoxynaphthyl group, dimethylnaphthyl group, methylfuryl group, methoxythienyl group, chlorothienyl group, methylthienyl group, methylpyrolyl group, chloropyrolyl group, methylpyridyl group, chloropyridyl group, dimethoxypyrimidinyl group, methylpyrimidinyl group, chloropyrimidinyl group, methylbenzofuryl group, methoxybenzofuryl group, chlorobenzofuryl group, methylbenzothienyl group, methylindolyl group, methylquinolyl group, methylthiazolyl group, methylpyrazolyl group, methyloxazolyl group and methylbenzooxazolyl group.

In the above formula (1), $R^2$ and $R^3$ are each independently a hydrogen atom or alkyl group having 1 to 12 carbon atoms, or $R^2$ and $R^3$ may be bonded together to form a ring with a carbon atom bonded thereto.

Examples of the alkyl group include methyl group, ethyl group, propyl group, butyl group, pentyl group, hexyl group, hepty group, octyl group, nonyl group and decyl group. The ring formed by $R^2$ and $R^3$ bonded together and the carbon atom bonded thereto is a cycloalkane ring such as cyclopentane ring or cyclohexane ring.

In the above formula (1), $R^4$ is a substituted or nonsubstituted alkyl group having 1 to 12 carbon atoms, substituted or nonsubstituted alkenyl group having 2 to 12 carbon atoms, substituted or nonsubstituted alkynyl group having 2 to 12 carbon atoms, substituted or nonsubstituted aryl group having 6 to 14 carbon atoms, substituted or nonsubstituted heteroaryl group having 3 to 8 carbon atoms, substituted or nonsubstituted cycloalkyl group having 3 to 6 carbon atoms, substituted or nonsubstituted cycloalkenyl group having 4 to 6 carbon atoms, or substituted or nonsubstituted heterocycloalkyl group having 4 to 5 carbon atoms.

Examples of the above alkyl group include methyl group, ethyl group, propyl group, butyl group, pentyl group, hexyl group, heptyl group, octyl group, nonyl group and decyl group. Examples of the alkenyl group include propenyl group, butenyl group, pentenyl group, hexenyl group or octenyl group. Examples of the alkynyl group include propynyl group and butynyl group. Examples of the aryl group include phenyl group, naphthyl group, anthranyl group and phenanthrenyl group. Examples of the heteroaryl group include furyl group, thienyl group, pyrrolyl group, pyridyl group, pyrimidinyl group, benzofuryl group, benzothienyl group, indolyl group, quinolyl group, thiazolyl group, pyrazolyl group, oxazolyl group and benzoxazolyl group. Examples of the cycloalkyl group include cyclopropyl group, cyclobutyl group, cyclopentyl group, cyclohexyl group and cycloheptyl group. Examples of the cycloalkenyl group include cyclopentenyl group, cyclohexenyl group. Examples of the heterocycloalkyl group include tetrahydrofuryl group, tetrahydrothienyl group and pyrrolidyl group.

Exmples of the substituent of the substituted alkyl group, substituted alkenyl group and substituted alkynyl group include halogen atoms such as chlorine atom, bromine atom, iodine atom and fluorine atom; alkoxy groups such as methoxy group, ethoxy group, propoxy group and butoxy group; alkylthio groups such as methylthio group, ethylthio group and propylthio group; aryl groups such as phenyl group; aryloxy groups such as phenoxy group; cyano group; nitro group; amino group; N,N-dialkylamino groups such as N,N-dimethylamino group and N,N-diethylamino group; alkoxycarbonyl groups such as methoxycarbonyl group and ethoxycarbonyl group.

Illustrative examples of the above substituted alkyl group include fluoromethyl group, trifluoromethyl group, chloromethyl group, chloroethyl group, bromoethyl group, chloropropyl group, chlorohexyl group, methoxymethyl group, methoxyethyl group, methoxypropyl group, methoxybutyl group, ethoxymethyl group, ethoxyethyl group, ethoxypropyl group, butoxymethyl group, butoxyethyl group, phenoxymethyl group, phenoxyethyl group, cyanopropyl group, cyanobutyl group, nitroethyl group, nitropropyl group, ethylthiomethyl group, propiothiomethyl group, methylthioethyl group, ethylthioethyl group, N,N-diethylaminoethyl group, N,N-diethylaminopropyl group, phenylmethyl group, phenylethyl group, methoxythienylmethyl group, methoxycarbonylmethyl group, methoxycarbonylethyl group and ethoxycarbonylethyl group. Examples of the substituted alkenyl group include chloropropenyl group, cyanobutenyl group and methoxypentenyl group. Examples of the substituted alkinyl group include chloropentynyl group, ethoxybutynyl group and nitrohexynyl group.

Examples of the substituent of the substituted aryl group, substituted heteroaryl group, substituted cycloalkyl group, substituted cycloalkenyl group and substituted heterocycloalkyl group include alkyl groups such as methyl group, ethyl group and propyl group; halogen atoms such as chlorine atom, bromine atom, iodine atom and fluorine atom; haloalkyl groups such as chloromethyl group and trifluoromethyl group; alkoxy groups such as methoxy group, ethoxy group and propoxy group; alkylthio groups such as methylthio group, ethylthio group and propylthio group; alkoxyalkyl groups such as methoxymethyl group and ethoxymethyl group; cyano group; nitro group; amino group; and N,N-dialkylamino groups such as N,N-dimethylamino group and N,N-diethylamino group.

Illustrative examples of the substituted aryl group, substituted heteroaryl group, substituted cycloalkyl group, substituted cycloalkenyl group and substituted heterocycloalkyl group include methylphenyl group, ethylphenyl group, propylphenyl group, butylphenyl group, hexylphenyl group, dimethylphenyl group, ethyl(methyl)phenyl group, ethyl(propyl)phenyl group, chlorophenyl group, bromophenyl group, fluorophenyl group, dichlorophenyl group, methoxyphenyl group, ethoxyphenyl group, propoxyphenyl group, dimethoxyphenyl group, cyanophenyl group, nitrophenyl group, chloro(methyl)phenyl group, methoxy(methyl)phenyl group, methylthiophenyl group, (trifluoromethyl)phenyl group, (dimethyl)aminophenyl group, chloro(nitro)phenyl group, methylnaphthyl group, chloronaphthyl group, methoxynaphthyl group, dimethylnaphthyl group, methylfuryl group, methoxythienyl group, chlorothienyl group, methylthienyl group, methylpyrolyl group, chloropyrolyl group, methylpyridyl group, chloropyridyl group, dimethoxypyrimidinyl group, methylpyrimidinyl group, chloropyrimidinyl group, methylbenzofuryl group, methoxybenzofuryl group, chlorobenzofuryl group, methylbenzothienyl group, methylindolyl group, methylquinolyl group, methylthiazolyl group, methylpyrazolyl group, methyloxazolyl group, methylbenzooxazolyl group, chloroethenyl group, bromoethenyl group, chloropropenyl group, chlorohexenyl group, methylcyclopropyl group, ethylcyclopropyl group, chlorocyclopropyl group, methoxycyclopropyl group, methylcyclopentyl group, chlorocyclohexyl group, methylcyclohexyl group, methylcyclopentenyl group, chlorocyclohexenyl group, methylcyclohexenyl group, N-methylpyrrolidyl group and N-ethylpyrrolidyl group.

In the above formula (1), $R^5$ is a substituted or nonsubstituted heteroaryl group having 3 to 8 carbon atoms and containing 1 to 2 hetero atoms selected from the group consisting of oxygen atom, sulfur atom and nitrogen atom, substituted or nonsubstituted aryl group having 6 to 14 carbon atoms, or substituted or nonsubstituted alkyl group having 1 to 12 carbon atoms.

Examples of the substituted or nonsubstituted heteroaryl group, substituted or nonsubstituted aryl group, or substituted or nonsubstituted alkyl group are the same as those listed for $R^4$.

Although there are isomers of the compounds having the above groups in most cases, all the isomers may be used in the composition of the present invention without restriction. For example, when a certain group is a methylphenyl group, the group may be o-methylphenyl group, m-methylphenyl group or p-methylphenyl group. When a certain group is a butyl group, the group may be n-butyl group, s-butyl group or t-butyl group.

The ethenylamide compound represented by the above formula (1) can be produced by various methods. For example, it is produced by an addition reaction between a Schiff base represented by the following formula (4):

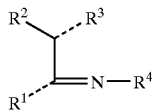
(4)

and an acid halide represented by the following formula (5):

and the subsequent elimination reaction of hydrogen halide. The formed ethenylamide compound contains the acid halide used as a raw material and hydrogen halide by-produced by the production process as impurities in small quantities (specifically, 0.01 to 2 wt % of the ethenylamide compound). Since the type and amount of the acidic component contained in the ethenylamide compound which can be acquired differ according to a reaction system, they cannot be specified unconditionally. However, the existence of the acidic component can be easily confirmed by measuring pH and the amount thereof can be determined by neutralization titration. When an ethenylamide compound containing this acidic component as an impurity is used in the present invention, its effect can be exhibited the most advantageously. If the acidic component can be completely removed by purification, an emulsion having high keeping stability can be obtained but a loss of the ethenylamide compound is produced at the time of a high level of purification. Even when an unpurified ethenylamide compound is used, an emulsion having high keeping stability can be obtained simply by adding a third component.

Examples of the ethenylamide compound which can be advantageously used in the present invention include
2-chloro-N-(2-ethoxyethyl)-N-(2-methyl-1-phenyl-1-propenyl)acetamide (No. 1 compound in the following Examples, the numerals within the parentheses are compound numbers in the Examples),
2-chloro-N-(2-methoxyethyl)-N-(2-methyl-1-phenyl-1-propenyl)acetamide (No. 2),
2-chloro-N-(2,6-dimethylphenyl)-N-(1-phenylethenyl) acetamide (No. 3),
2-chloro-N-(2-ethoxyethyl)-N-(1-phenyl-1-propenyl) acetamide (No. 4),
N-(3-methoxypropyl)-N-(2-methyl-1-(4-methylphenyl)-1-propenyl)acetamide (No. 5),
2-bromo-N-pentyl-N-(1-(3-chlorophenyl)ethenyl)acetamide (no. 6),
2-methyl-N-(3-ethoxypropyl)-N-(2-methyl-1-(4-methoxyphenyl)-1-propenyl)propylamide (No. 7),
2-chloro-N-phenyl-N-(2-methyl-1-(4-methylthiophenyl)-1-butenyl)acetamide (No. 8),
N-(3-propoxyproyl)-N-(2-methyl-1-(4-cyanophenyl)-1-propenyl)benzamide (No. 9),
4-ethyl-N-(2-thienyl)-N-(1-(1-naphthyl)-1-butenyl) benzamide (No. 10),
4-methoxy-N-ethyl-N-(2-methyl-1-(2-pyridyl)-1-propenyl) benzamide (No. 11),
2-methxoy-N-butyl-N-(2-methyl-1-(2-thienyl)-1-propenyl) acetamide (No. 12),
2-chloro-N-(2-4-methoxythienyl)-N-(2-methyl-1-(2-furyl)-1-propenyl)acetamide (No. 13),
2-chloro-N-(2,4-dichlorophenyl)-N-(1-phenylethenyl) acetamide (No. 14),
2-bromo-N-methoxymethyl-N-(1-(2,4-dimethylphenyl)-1-propenyl)acetamide (No. 15),
2-chloro-N-(2,6-dimethylphenyl)-N-(1-(N-methylpyrimidinyl)ethenyl)acetamide (No. 16),
N-(1-naphthyl-N-(2-methyl-1-(4-bromophenyl)-1-propenyl)propylamide (No. 17),
2,2,2-trifluoro-N-(2-methylthioethyl)-N-(1-(4-isopropylphenyl)-1-pentenyl)acetamide (No. 18),
N-(2-ethoxycarbonylethyl)-N-(1-(2-(4-methoxythionyl)) ethenylbenzamide (No. 19) and
N-ethyl-N-(1-(4-nitrophenyl)-2-cyclohexylethenyl) thiazoamide (No. 20).

They may be used alone or in combination of two or more as a herbicidally active component.

The amount of the ethenylamide compound contained in the herbicidal emulsion composition of the present invention is not particularly limited. However, if it is too small, the amount of an emulsion to be applied to a field increases. Therefore, it is preferably 30 to 90 wt %, particularly preferably 50 to 80 wt % based on the total weight of the ethenylamide compound, the dichloroacetamide compound, amino alcohol and polar nonaqueous solvent.

The herbicidal emulsion composition of the present invention contains a dichloroacetamide compound represented by the above formula (2) or (3) as a phytotoxicity reducing agent. The phytotoxicity reducing agent is a compound which has the effect of reducing phytotoxicity caused by a herbicidally active component and lightens or detoxifies phytotoxicity without impairing the effect of the herbicidally active component and still has the effect of protecting cultivated crops. Therefore, the term "phytotoxicity reducing agent" as used herein includes counter-agents, antidotes and safeners.

A description is subsequently given of the dichloroacetamide compounds represented by the above formulas (2) and (3).

In the above formula (2), $R^6$ and $R^7$ are each independently a hydrogen atom or alkyl group having 1 to 3 carbon atoms. Examples of the alkyl group include methyl group, ethyl group, n-propyl group and isopropyl group.

In the above formula (2), $R^8$ is a hydrogen atom, alkyl group having 1 to 3 carbon atoms, or substituted or nonsubstituted heteroaryl group having 3 to 8 carbon atoms and containing 1 to 2 hetero atoms selected from the group consisting of oxygen atom, sulfur atom and nitrogen atom. Specific examples of the above alkyl group are the same as those listed for $R^6$ and $R^7$. Examples of the substituted or nonsubstituted heteroaryl group are the same as those listed for $R^1$.

Out of the dichloroacetamide compounds represented by the above formula (2), preferred are
2,2,5-trimethyl-3-dichloroacetyloxazolidine (compound A in the following Examples, the symbols within the parentheses are compound symbols in the Examples),
2,2-dimethyl-3-dichloroacetyloxazolidine (B),
2-ethyl-2-methyl-3-dichloroaetyloxazolidine (C),
2,2-dimethyl-5-(2-furyl)-3-dichloroacetyloxazolidine (D) and
2-methyl-5-(2-(4-methylfuryl))-3-dichlorooxazolidine (E).

Out of the dichloroacetamide compounds represented by the above formula (2), particularly preferred are compounds of the formula (2) in which $R^6$, $R^7$ and $R^8$ are each independently a hydrogen atom or methyl group (the above compounds A and B) from the large effect of reducing phytotoxicity, the easy acquisition of raw materials and production ease.

$R^9$, $R^{10}$ and $R^{11}$ in the above formula (3) are each independently a hydrogen tom or alkyl group having 1 to 2 carbon atoms, namely, methyl group or ethyl group, n is an integer of 2 or 3, and m is 0 or 1.

Out of the dichloroacetamide compounds represented by the above formula (3), preferred are
5-dichloroacetyl-3,3,6-trimethyl-9-oxo-1,5-diazabicyclo [4.3.0]nonane (compound F in Examples to be described hereinafter, symbols within the parentheses indicate compounds in Examples),
4-dichloroacetyl-5-methyl-9-oxo-1,4-diazabicyclo[3.4.0] nonane (G),
4-dichloroacetyl-9-oxo-1,5-diazabicyclo[3.4.0]nonane (H),
5-dichloroacetyl-6-ethyl-9-oxo-1,5-diazabicyclo[4.3.0] nonane (I), and
5-dichloroacetyl-3,3,6-trimethyl-10-oxo-1,5-azabicyclo [4.4.0]decane (J).

Out of the dichloroacetamide compounds represented by the above formula (3), particularly preferred are compounds of the formula (3) in which $R^9$, $R^{10}$ and $R^{11}$ are each independently a hydrogen atom or methyl group (the above compound F) from the large effect of reducing phytotoxicity, the easy acquisition of raw materials and production ease.

The dichloroacetamide compounds may be used alone or in combination of two or more as the phytotoxicity reducing agent.

The mixing ratio of the above dichloroacetamide compound to the ethenylamide compound in the herbicidal emulsion composition of the present invention is not particularly limited and may be suitably determined according to the types and amounts of the compounds and cultivation environments such as a cultivation crop and soil. Generally speaking, the dichloroacetamide compound is preferably used in an amount of 0.01 to 1 part by weight based on 1 part by weight of the ethenylamide compound. The content of the dichloroacetamide compound in the herbicidal emulsion composition of the present invention is preferably 3 to 45 wt %, particularly preferably 5 to 20 wt % based on the total weight of the ethenylamide compound, dichloroacetamide compound, amino alcohol and polar nonaqueous solvent.

The most outstanding feature of the herbicidal emulsion composition of the present invention is that it contains an amino alcohol and a polar nonaqueous solvent in addition to the above herbicidally active component and phytotoxicity reducing agent. By containing these component, the decomposition of the dichloroacetamide compound as a phytotoxicity reducing agent is prevented, the phytotoxicity reducing effect is not lowered even when it is kept for a long time and crystals do not deposit.

Any known amino alcohol may be used with no limitation. Preferred example of the amino alcohol include ethanolamine, 1-amino-2-propanol (isopropanolamine), 2-amno-1-propanol, 3-amino-1-propanol, 1-amino-2-butanol, 2-amino-1-butanol, 4-amino-1-butanol, 2-amino-2-methyl-1-propanol, diethanolamine, triethanolamine, diisopropanolamine and triisopropanolamine. Out of these, ethanolamine and 1-amno-2-propanolamine (isopropanolamine) are particularly preferred from the economical point of view. These amino alcohols may be used alone or in combination of two or more.

The amount of the amino alcohol used in the herbicidal emulsion composition of the present invention is not particularly limited and is sufficient to prevent the decomposition of the phytotoxicity reducing agent by forming a salt with an acidic component contained in the herbicidally active component, for example, preferably 0.1 to 2 mols, more preferably 0.5 to 1.5 mols based on 1 mol of the acidic component. The amount of the amino alcohol in the herbicidal emulsion composition of the present invention is preferably 0.1 to 5 wt %, particularly preferably 0.5 to 2 wt % based on the total weight of the ethenylamide compound, dichloroacetamide compound, amino alcohol and polar nonaqueous solvent.

Any known polar nonaqueous solvent may be used with no limitation. Preferred examples of the polar nonaqueous solvent include nitrogen-containing solvents such as N-methyl-2-pyrrolidone, N,N-dimethylformamide, hexamethylphosphoric acid triamide; ketones such as acetone, methyl ethyl ketone, diisobutyl ketone, cyclohexanone, acetophenone and isophorone; esters such as ethyl acetate, amyl acetate, ethylene glycol acetate, butyl maleate and diethyl succinate; and alcohols such as methanol, n-hexanol, ethylene glycol and diethylene glycol. These polar nonaqueous solvents may be used alone or in combination of two or more.

Out of these, nitrogen-containing solvents such as N-methyl-2-pyrrolidone, N,N-dimethylformamide, and hexamethylphosphoric acid triamide are particularly preferred because they have strong power to dissolve the ethenylamide compound, dichloroacetamide compound and a salt formed from the acidic component and amino alcohol and can provide a highly concentrated emulsion.

The content of the polar nonaqueous solvent in the herbicidal emulsion composition of the present invention is not particularly limited and may be sufficient to dissolve the formed salt. However, it is preferably 5 to 80 wt % based on the total weight of the ethenylamide compound, dichloroacetamide compound, amino alcohol and polar nonaqueous solvent. When the polar nonaqueous solvent is used excessively, the content of the ethenylamide compound or dichloroacetamide compound becomes small, thereby increasing the amount of the emulsion applied to the field. Therefore, it is more preferably 10 to 40 wt %.

The herbicidal emulsion composition of the present invention may contain components other tan the above essential ingredients, such as a surfactant and nonpolar solvent in limits not prejudicial to the effect of the present invention.

The surfactant used in the herbicidal emulsion composition of the present invention is a nonionic, cationic, anionic or amphoteric surfactant. In general, a nonionic and/or anionic surfactant are/is preferably used. Preferred examples of the nonionic surfactant include surfactants obtained by addition polymerizing a higher alcohol such as lauryl alcohol, stearyl alcohol or oleyl alcohol with ethylene oxide; surfactants obtained by addition polymerizing an alkylphenol such as isooctylphenol or nonylphenol with ethylene oxide; surfactants obtained by addition polymerizing an alkylnaphthol such as butylnaphthol or octylnaphthol with ethylene oxide; surfactants obtained by addition polymerizing a higher fatty acid such as palmitic acid, stearic acid or oleic acid with ethylene oxide; surfactants obtained by addition polymerizing stearyl phosphoric acid, dilauryl phosphoric acid or dialkylphosphoric acid with ethylene oxide; surfactants obtained by addition polymerizing an amine such as dodecylamine or acid amide such as stearic acid amide with ethylene oxide; surfactants obtained by addition polymerizing a higher fatty acid ester of a polyhydric alcohol such as sorbitan with ethylene oxide; surfactants obtained by addition polymerizing ethylene oxide with propylene oxide; and esters of a polyhydric aliphatic acid such as dioctyl succinate and an alcohol.

Preferred examples of the anionic surfactant include alkyl sulfuric acid ester salts such as sodium lauryl sulfate and oleyl alcohol sulfuric acid ester amine salts; alkyl sulfonic acid salts such as sulfosuccinic acid dioctyl ester sodium and 2-ethylhexane sulfonic acid sodium; aryl sulfonic acid salts such as isopropylnaphthalene sulfonic acid sodium, methylene bisnaphthalene sulfonic acid sodium, lignin sulfonic acid sodium, dodecylbenzene sulfonic acid sodium and dodecylbenzene sulfonic acid calcium, and phosphoric acid salts such as sodium tripolyphosphate.

The amount of the surfactant to be added to the herbicidal emulsion composition of the present invention is not particularly limited and may be sufficient to keep a stable emulsion state when it is diluted with water at the time of spraying. In general, it is preferably 2 to 20 parts by weight based on 100 parts by weight of the total of the ethenylamide compound, dichloroacetamide compound, amino alcohol and polar nonaqueous solvent.

A nonpolar solvent may be used as the solvent to improve the stability of an emulsion state when it is diluted with water at the time of spraying the herbicidal emulsion composition, in addition to the polar nonaqueous solvent.

Examples of the nonpolar solvent include aromatic hydrocarbons such as benzene, toluene, xylene, ethylbenzene, coumene and methyl naphthalene; and paraffin-based or naphthene-based hydrocarbons such as kerosene, mineral oil, spindle oil and white oil.

The content of the nonpolar solvent in the herbicidal emulsion composition of the present invention is not particularly limited. In general, it is preferably 0 to 50 parts by weight based on 100 parts by weight of the total of the ethenylamide compound, dichloroacetamide compound, amino alcohol and polar nonaqueous solvent. When the nonpolar solvent is used excessively, the content of the ethenylamide compound or the dichloroacetamide compound becomes low, whereby the content of an emulsion applied for the field is increased. Therefore, it is preferably 0 to 20 parts by weight.

The procedure of preparing the herbicidal emulsion composition of the present invention is not particularly limited. Describing a specific preparation procedure, predetermined amounts of the ethenylamide compound, dichloroacetamide compound, amino alcohol and polar nonaqueous solvent and optionally a surfactant are added and mixed together to prepare an emulsion.

To apply the composition to a field, the herbicidal emulsion composition is diluted with water to 50 to 2,000 times and optionally a surfactant is added to the resulting solution and sprayed over the entire surface of the field by pressure.

The amount of the herbicidal emulsion composition of the present invention is 2 to 5,000 g, preferably 10 to 2,000 g per 1 ha in terms of the ethenylamide compound.

EXAMPLES

The following examples are provided for the purpose of further illustrating a hercidal emulsion composition the present invention but are in no way to be taken as limiting.

In Examples, compounds No. 1 to 20 shown in Tables 1 and 2 were used as the ethenylamide compound and compounds A to J shown in Tables 3 and 4 were used as the dichloroacetamide compound.

TABLE 1

| No | $R^1$ | $R^2$ | $R^3$ | $R^4$ | $R^5$ |
|---|---|---|---|---|---|
| 1 | phenyl | $CH_3$ | $CH_3$ | $CH_2CH_2OC_2H_5$ | $CH_2Cl$ |
| 2 | phenyl | $CH_3$ | $CH_3$ | $CH_2CH_2OCH_3$ | $CH_2Cl$ |
| 3 | phenyl | H | H | 2,6-dimethylphenyl | $CH_2Cl$ |
| 4 | phenyl | H | $CH_3$ | $CH_2CH_2OC_2H_5$ | $CH_2Cl$ |
| 5 | 4-methylphenyl | $CH_3$ | $CH_3$ | $(CH_2)_3OCH_3$ | $CH_3$ |

TABLE 1-continued
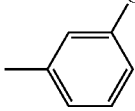
| No | R¹ | R² | R³ | R⁴ | R⁵ |
|----|----|----|----|----|----|
| 6 | 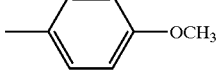 | H | H | $(CH_2)_4CH_3$ | $CH_2Br$ |
| 7 | 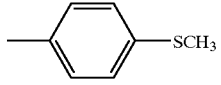 | $CH_3$ | $CH_3$ | $(CH_2)_3OC_2H_5$ | $CH(CH_3)_2$ |
| 8 | 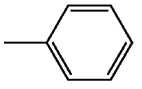 | $CH_3$ | $C_2H_5$ | 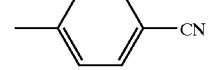 | $CH_2Cl$ |
| 9 | 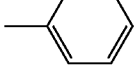 | $CH_3$ | $CH_3$ | $(CH_2)_3OC_3H_7$ | 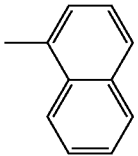 |
| 10 | 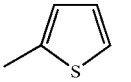 | $C_2H_5$ | H | 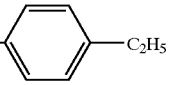 | 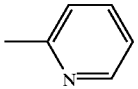 |
TABLE 2
| No | R¹ | R² | R³ | R⁴ | R⁵ |
|----|----|----|----|----|----|
| 11 |  | $CH_3$ | $CH_3$ | $C_2H_5$ | 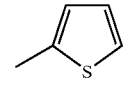 |
| 12 | 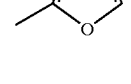 | $CH_3$ | $CH_3$ | $(CH_2)_3CH_3$ | $CH_2OCH_3$ |
| 13 | 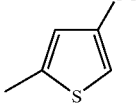 | $CH_3$ | $CH_3$ | 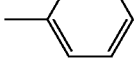 | $CH_2Cl$ |
| 14 | 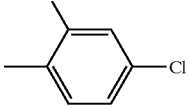 | H | H | 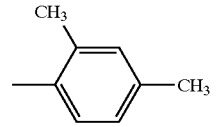 | $CH_2Cl$ |
| 15 |  | $CH_3$ | H | $CH_2OCH_3$ | $CH_2Br$ |

TABLE 2-continued

| No | R¹ | R² | R³ | R⁴ | R⁵ |
|---|---|---|---|---|---|
| 16 | 1,2-dimethylpyrrol-5-yl | H | H | 2,3-dimethylphenyl | $CH_2Cl$ |
| 17 | 4-bromophenyl | $CH_3$ | $CH_3$ | 1-naphthyl | $C_2H_5$ |
| 18 | 4-isopropylphenyl | | H | $C_3H_7$ | $(CH_2)_2SCH_3$ | $CF_3$ |
| 19 | 4-methoxy-2-methylthiophen-5-yl | H | H | $C_2H_4CO_2C_2H_5$ | phenyl |
| 20 | 4-nitrophenyl | —$(CH_2)_5$— | | $C_2H_5$ | 2-methylthiophen-5-yl |

TABLE 3

$$\text{structure with } R^6, R^7 \text{ on carbon adjacent to O; N-COCHCl}_2; R^8 \text{ on other carbon of oxazolidine ring}$$

| symbol | R⁶ | R⁷ | R⁸ |
|---|---|---|---|
| A | $CH_3$ | $CH_3$ | $CH_3$ |
| B | $CH_3$ | $CH_3$ | H |
| C | $C_2H_5$ | $CH_3$ | H |
| D | $CH_3$ | $CH_3$ | 2-methylfuran-5-yl |
| E | H | $CH_3$ | 2,5-dimethylfuran-3-yl |

TABLE 4

$$\text{cyclic diamide structure: } O=C-(CH_2)_n-C(R^9)-N-COCHCl_2, \text{ with } (CH_2)_m \text{ and } R^{10}, R^{11}$$

| symbol | R⁹ | R¹⁰ | R¹¹ | n | m |
|---|---|---|---|---|---|
| F | $CH_3$ | $CH_3$ | $CH_3$ | 2 | 1 |
| G | $CH_3$ | H | H | 3 | 0 |
| H | H | H | H | 3 | 0 |
| I | $C_2H_5$ | H | H | 2 | 1 |
| J | $CH_3$ | $CH_3$ | $CH_3$ | 3 | 1 |

Example 1

Preparation Example 1

16.5 parts by weight of N-methyl-2-pyrrolidone was added to 60 parts by weight of the ethenylamide compound No. 1 shown in Table 1, 7.5 parts by weight of the dichloroacetamide compound A shown in Table 3, 10 parts by weight of polyoxyethylene allylphenyl ether surfactant, 5 parts by weight of calcium dodecylbenzenesulfonate surfactant and 1 part by weight of 1-amino-2-propanol and well mixed with them to prepare a herbicidal emulsion composition.

The physical properties of the above herbicidal emulsion composition were evaluated in accordance with the following methods.

<Decomposition Rate of Dichloroacetamide Compound>

The content of the dichloroacetamide compound in the herbicidal emulsion composition was analyzed by high-speed liquid chromatography (HPLC) (A %). This herbicidal emulsion composition was charged into a closed vessel and kept in a thermostat at 50° C. for 30 days and then the content of the dichloroacetamide compound was analyzed by HPLC (B %). The decomposition rate of the dichloroacetamide compound was calculated from the following equation. The keeping conditions (50° C., 30 days) were set based on the assumption that it would be kept at room temperature for 3 years. Decomposition rate of dichloroacetamide compound (%)=(1−B/A)×100

<Existence of Crystal Deposition>

After the herbicidal emulsion composition was placed in a closed vessel and kept in a thermostat at −5° C. for 30 days, the deposition of crystals was observed visually. The temperature of −5° C. was based on the assumption that it would be kept in winter.

The results are shown in Table 5.

TABLE 5

| P. Ex. | decomposition rate of dichloroacetamide compound (%) | crystal deposition |
|---|---|---|
| 1 | 0 | Not seen |
| 2 | 0 | Not seen |
| 3 | 0 | Not seen |
| 4 | 0 | Not seen |
| 5 | 0 | Not seen |
| 6 | 0 | Not seen |
| 7 | 0 | Not seen |
| 8 | 0 | Not seen |
| 9 | 0 | Not seen |
| 10 | 0 | Not seen |
| 11 | 0 | Not seen |
| 12 | 0 | Not seen |
| 13 | 0 | Not seen |

TABLE 5-continued

| P. Ex. | decomposition rate of dichloroacetamide compound (%) | crystal deposition |
|---|---|---|
| 14 | 0 | Not seen |
| 15 | 0 | Not seen |

P. Ex.: Preparation example test example 1 (herbicidal activity and phytotoxicity to corn)

The herbicidal activities and phytotoxicities to corn of the above herbicidal emulsion composition which was prepared after less than 1 day (I) and the herbicidal emulsion composition which was kept in a thermostat at 50° C. for 30 days and then kept in a thermostat at −5° C. for 30 days (II) were evaluated in accordance with the following methods.

That is, a plastic vessel (35 cm in length×18 cm in width×14 cm in height) was filled with soil (containing 20% of sand to observe the effect of phytotoxicity easily), corn seeds were sowed to a depth of 3 cm, and seeds of weeds (*Digitaria ciliaris, Poa annua, Echinochloa crus-galli, Chenopodium album* and *Galisoga ciliata*) were also sowed to a depth of 1 cm. After the seeds were covered with soil, the herbicidal emulsion composition equivalent to 1,500 g of the ethenylamide compound (188 g of the dichloroacetamide compound) per 1 ha was diluted with water to 1,000 times and the resulting solution was sprayed to the surface of the soil by a spray. These seeds were grown in a greenhouse maintained at an average temperature of 25° C. and the herbicidal activity and phytotoxicity of the composition were evaluated in six grades from 0 to 5 after 2 weeks. That is, grade 5 is a weed suppression rate of 100% (=complete death), grade 4 is a weed suppression rate of 99 to 75%, grade 3 is a weed suppression rate of 74 to 50%, grade 2 is a weed suppression rate of 49 to 25%, grade 1 is a weed suppression rate of 24 to 1% and grade 0 is a weed suppression rate of 0% (no herbicidal activity or no phytotoxicity). Control 1 shown herein was a herbicidal emulsion composition which contained only compound No. 1 and no phytotoxicity reducing agent.

The results are shown in Table 6. As shown in Table 6, phytotoxicity was reduced compared with Control 1 which contained no phytotoxicity reducing agent and kept its effect after long-term storage.

TABLE 6

| | | herbicidal activity | | | | | |
|---|---|---|---|---|---|---|---|
| P. Ex. | keeping conditions | *Digitaria ciliaris* | *Poa annua* | *Echinochloa crus-galli* | *Chenopodium album* | *Galisoga ciliata* | phytotoxicity corn |
| 1 | I | 5 | 5 | 5 | 4 | 4 | 0 |
|   | II | 5 | 5 | 5 | 4 | 4 | 0 |
| 2 | I | 5 | 5 | 5 | 4 | 4 | 0 |
|   | II | 5 | 5 | 5 | 4 | 4 | 0 |
| 3 | I | 5 | 5 | 5 | 4 | 4 | 0 |
|   | II | 5 | 5 | 5 | 4 | 4 | 0 |
| 4 | I | 5 | 5 | 4 | 4 | 4 | 0 |
|   | II | 5 | 5 | 4 | 4 | 4 | 0 |
| 5 | I | 5 | 5 | 4 | 4 | 4 | 0 |
|   | II | 5 | 5 | 4 | 4 | 4 | 0 |
| 6 | I | 5 | 4 | 4 | 4 | 3 | 0 |
|   | II | 5 | 4 | 4 | 4 | 3 | 0 |
| 7 | I | 5 | 4 | 4 | 4 | 3 | 0 |
|   | II | 5 | 4 | 4 | 4 | 3 | 0 |
| 8 | I | 5 | 4 | 4 | 4 | 4 | 0 |
|   | II | 5 | 4 | 4 | 4 | 4 | 0 |

TABLE 6-continued

| P. Ex. | keeping conditions | Digitaria ciliaris | Poa annua | Echinochloa crus-galli | Chenopodium album | Galisoga ciliata | phytotoxicity corn |
|---|---|---|---|---|---|---|---|
| | | | | herbicidal activity | | | |
| 9 | I | 5 | 4 | 4 | 4 | 4 | 0 |
| | II | 5 | 4 | 4 | 4 | 4 | 0 |
| 10 | I | 4 | 5 | 4 | 4 | 3 | 0 |
| | II | 4 | 5 | 4 | 4 | 3 | 0 |
| 11 | I | 4 | 5 | 4 | 4 | 3 | 0 |
| | II | 4 | 5 | 4 | 4 | 3 | 0 |
| 12 | I | 4 | 5 | 4 | 4 | 3 | 0 |
| | II | 4 | 5 | 4 | 4 | 3 | 0 |
| 13 | I | 4 | 5 | 4 | 4 | 3 | 0 |
| | II | 4 | 5 | 4 | 4 | 3 | 0 |
| 14 | I | 4 | 5 | 4 | 4 | 4 | 0 |
| | II | 4 | 5 | 4 | 4 | 4 | 0 |
| 15 | I | 4 | 5 | 4 | 4 | 4 | 0 |
| | II | 4 | 5 | 4 | 4 | 4 | 0 |
| Control 1 | I | 5 | 5 | 5 | 4 | 4 | 3 |

P. Ex.: Preparation example
Note) keeping conditions
I: used in this test less than 24 hours after preparation
II: used in this test after it was kept at 50° C. for 30 days and then kept at −5° C. for 30 days

Example 2

10 parts by weight of N-methyl-2-pyrrolidone and 6.5 parts by weight of methyl naphthalene were added to 60 parts by weight of the ethenylamide compound No. 1 shown in Table 1, 7.5 parts by weight of the dichloroacetamide compound A shown in Table 3, 10 parts by weight of polyoxyethylene allylphenyl ether surfactant, 5 parts by weight of calcium dodecylbenzenesulfonate and 1 part by weight of ethanolamine and mixed together to prepare a herbicidal emulsion composition (preparation example 2) and the obtained herbicidal emulsion composition was evaluated in the same manner as test example 1 (test example 2). The results are shown in Table 5 and Table 6. It is understood that the keeping stability of this herbicidal emulsion composition was excellent.

Examples 3 to 15

The herbicidal emulsion compositions of Preparation examples 3 to 15 shown in Table 7 were prepared (preparation examples 3 to 15).

TABLE 7

| P. Ex. | herbicidally active component | phytotoxicity reducing agent | polar nonaqueous solvent |
|---|---|---|---|
| 1 | No. 1 60 | A 7.5 | N-methyl-2-pyrrolidone 16.5 |
| 2 | No. 1 60 | A 7.5 | N-methyl-2-pyrrolidone 10 |
| 3 | No. 1 60 | B 7.5 | N-methyl-2-pyrrolidone 16.5 |
| 4 | No. 2 60 | A 7.5 | N-methyl-2-pyrrolidone 10 |
| 5 | No. 2 60 | F 7.5 | dimethyl sulfoxide 16.5 |
| 6 | No. 3 60 | C 7.5 | N-methyl-2-pyrrolidone 10 |
| 7 | No. 3 60 | G 7.5 | N-methyl-2-pyrrolidone 16.5 |
| 8 | No. 4 60 | A 7.5 | N,N-dimethylformamide 10 |
| 9 | No. 4 60 | G 7.5 | N-methyl-2-pyrrolidone 16.5 |
| 10 | No. 10 60 | A 7.5 | N-methyl-2-pyrrolidone 10 |
| 11 | No. 10 60 | F 7.5 | N-methyl-2-pyrrolidone 16.5 |
| 12 | No. 15 60 | A 7.5 | N-methyl-2-pyrrolidone 16.5 |
| 13 | No. 15 60 | H 7.5 | hexamethylphosphoric acid triamide 10 |
| 14 | No. 18 60 | C 7.5 | N-methyl-2-pyrrolidone 16.5 |
| 15 | No. 18 60 | I 7.5 | amyl acetate 10 |

| P. Ex. | amino alcohol | surfactant | nonpolar solvent |
|---|---|---|---|
| 1 | 1-amino-2-propanol 1 | polyoxyethylene allylphenyl ether 10 + calcium dodecyl- benzenesulfonate 5 | Not seen |
| 2 | 1-amino-2-propanol 1 | | methyl naphthalene 6.5 |
| 3 | ethanolamine 1 | | Not seen |
| 4 | ethanolamine 1 | | methyl naphthalene 6.5 |
| 5 | 1-amino-2-propanol 1 | | Not seen |
| 6 | ethanolamine 1 | | methyl naphthalene 6.5 |
| 7 | 1-amino-2-propanol 1 | | Not seen |
| 8 | ethanolamine 1 | | xylene 6.5 |
| 9 | 1-amino-2-propanol 1 | | Not seen |
| 10 | 1-amino-2-propanol 1 | | xylene 6.5 |
| 11 | ethanolamine 1 | | Not seen |
| 12 | 1-amino-2-propanol 1 | | Not seen |
| 13 | 1-amino-2-propanol 1 | | methyl naphthalene 6.5 |
| 14 | ethanolamine 1 | | Not seen |
| 15 | ethanolamine 1 | | xylene 6.5 |

P. Ex.: Preparation example
Note) Numerals indicate parts by weight in the herbicidal emulsion composition.

The prepared herbicidal emulsion compositions were evaluated in the same manner as in Test Example 1 (Test Examples 3 to 15). The results are shown in Tables 5 and 6. It is understood that all the herbicidal emulsion compositions had excellent keeping stability.

Comparative Examples 1 to 3

The herbicidal emulsion compositions shown in Table 8 were prepared and evaluated in the same manner as in Test Example 1. The results are shown in Tables 9 and 10.

TABLE 8

| P. Ex. | herbicidally active component | phytotoxicity reducing agent | polar nonaqueous solvent |
|---|---|---|---|
| 1 | No. 1 60 | A 7.5 | N-methyl-2-pyrrolidone 17.5 |
| 2 | No. 1 60 | A 7.5 | N-methyl-2-pyrrolidone 16.5 |
| 3 | No. 1 60 | B 7.5 | Not seen |

| P. Ex. | amino alcohol | surfactant | nonpolar solvent |
|---|---|---|---|
| 1 | Not seen | polyoxyethylene allylphenyl ether 10 + calcium dodecylbenzenesulfonate 5 | Not seen |
| 2 | di-n-propylamine 1 | | Not seen |
| 3 | 1-amino-2-propanol 1 | | Not seen |

P. Ex.: Preparation example
Note) Numerals indicate parts by weight in the herbicidal emulsion composition.

TABLE 9

| C. Ex. | decomposition rate of dichloroacetamide compound (%) | crystal deposition |
|---|---|---|
| 1 | 21 | Not seen |
| 2 | 0 | Seen |
| 3 | 0 | Seen |

C. Ex.: Comparative Example

TABLE 10

| P. Ex. | keeping conditions | herbicidal activity | | | | | phytotoxicity corn |
| | | *Digitaria ciliaris* | *Poa annua* | *Echinochloa crus-galli* | *Chenopodium album* | *Galisoga ciliata* | |
|---|---|---|---|---|---|---|---|
| 1 | I | 5 | 5 | 5 | 4 | 4 | 0 |
|   | II | 5 | 5 | 5 | 4 | 4 | 2 |
| 2 | I | 5 | 5 | 5 | 4 | 4 | 0 |
|   | II | 2 | 2 | 2 | 1 | 1 | 0 |
| 3 | I | 5 | 5 | 5 | 4 | 4 | 0 |
|   | II | 2 | 2 | 2 | 1 | 1 | 0 |
| Control 1 | I | 5 | 5 | 5 | 4 | 4 | 3 |

P. Ex.: Preparation example
Note) keeping conditions
I: used in this test less than 24 hours after preparation
II: used in this test after it was kept at 50° C. for 30 days and then kept at −5° C. for 30 days The herbicidal emulsion composition of Comparative Example 1 was prepared without using 1-amino-2-propanol in Preparation Example 1. In this case, the dichloroacetamide compound A decomposed and a reduction in phytotoxicity reducing effect was seen. The herbicidal emulsion composition of Comparative Example 2 was prepared by using di-n-propylamine in place of 1-amino-2-propanol in Preparation Example 1. In this case, crystals separated out and a spray was blocked during the spray of the composition to be impossible to spray, thereby reducing herbicidal activity. In Comparative Example 3, a herbicidal emulsion composition was prepared by using methyl naphthalene in place of N-methyl-2-pyrrolidone in Preparation Example 1. In this case, crystals separated out and herbicidal activity lowered.

According to the present invention, there can be obtained a herbicidal emulsion composition which contains an ethenylamide compound as a herbicidally active component and dichloroacetamide compound as a phytotoxicity reducing agent and has excellent keeping stability without depositing crystals even when it is kept for a long time. That is, even when the herbicidal emulsion composition of the present invention is kept for a long time, it can exhibit the above herbicidal effect as it is (for example, without dissolving crystals to eliminate the blockage of a spray).

What is claimed is:

1. A herbicidal emulsion composition comprising:
   (A) a herbicidally active component which is an ethenylamide compound represented by the following formula (1):

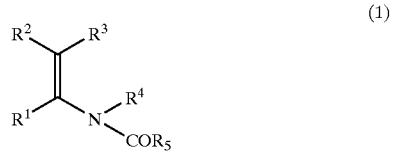

wherein $R^1$ is a substituted or nonsubstituted heteroaryl group having 3 to 8 carbon atoms and containing 1 to 2 hetero atoms selected from the group consisting of oxygen atom, sulfur atom and nitrogen atom, or substituted or nonsabstituted aryl group having 6 to 14 carbon atoms, $R^2$ and $R^3$ are each independently a hydrogen atom or alkyl group having 1 to 12 carbon atoms and may be bonded together to form a ring with a carbon atom bonded thereto, $R^4$ is a substituted or nonsubstituted alkyl group having 1 to 12 carbon atoms, substituted or nonsubstituted alkenyl group having 2 to 12 carbon atoms, substituted or nonsubstituted alkynyl group having 2 to 12 carbon atoms, substituted or nonsubstituted aryl group having 6 to 14 carbon atoms, substituted or nonsubstituted heteroaryl group having 3 to 8 carbon atoms, substituted or nonsubstituted cycloalkyl group having 3 to 6 carbon atoms, substituted or nonsubstituted cycloalkenyl group having 4 to 6 carbon atoms, or substituted or nonsubstituted heterocycloalkyl group having 4 to 5 carbon atoms, and $R^5$ is a substituted or nonsubstituted heteroaryl group having 3 to 8 carbon atoms and containing 1 to 2 hetero atoms selected from the group consisting of oxygen atom, sulfur atom and nitrogen atom, substituted or nonsubstituted aryl group having 6 to 14 carbon atoms, or substituted or nonsubstituted alkyl group having 1 to 12 carbon atoms, (B) a phytotoxicity reducing agent which is a dichloroacetamide compound represented by the following formula (2):

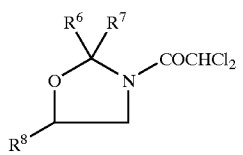

wherein $R^6$ and $R^7$ are each independently a hydrogen atom or alkyl group having 1 to 3 carbon atoms, and $R^8$ is a hydrogen atom, alkyl group having 1 to 3 carbon atoms, or substituted or nonsubstituted heteroaryl group having 3 to 8 carbon atoms and containing 1 to 2 hetero atoms selected from the group consisting of oxygen atom, sulfur atom and nitrogen atom, or the following formula (3):

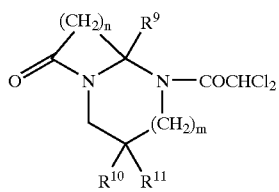

wherein $R^9$, $R^{10}$ and $R^{11}$ are each independently a hydrogen atom or alkyl group having 1 to 2 carbon atoms, n is 2 or 3, and m is 0 or 1, (C) an amino alcohol, and (D) a polar nonaqueous solvent.

2. The composition of claim 1, wherein the ethenylamide compound is a compound of the formula (1) in which $R^1$ is a substituted or nonsubstituted aryl group having 6 to 14 carbon atoms, $R^2$ and $R^3$ are each independently a hydrogen atom or alkyl group having 1 to 12 carbon atoms or may be bonded together to form a ring with a carbon atom bonded thereto, $R^4$ is a substituted or nonsubstituted alkyl group having 1 to 12 carbon atoms, and $R^5$ is a substituted or nonsubstituted alkyl group having 1 to 12 carbon atoms.

3. The composition of claim 1, wherein the dichloroacetamide compound is a compound of the formula (2) in which $R^6$, $R^7$ and $R^8$ are each independently a hydrogen atom or methyl group or a compound of the formula (3) in which $R^9$, $R^{10}$ and $R^{11}$ are each independently a hydrogen atom or methyl group.

4. The composition of claim 1, wherein the ethenylamide compound contains an acidic component as an impurity.

5. The composition of claim 1, wherein the content of the ethenylamide compound is 30 to 90 wt % based on the total weight of the herbicidal emulsion composition.

6. The composition of claim 1, wherein the content of the dichloroacetamide compound is 3 to 45 wt % based on the total weight of the herbicidal emulsion composition.

7. The composition of claim 1, wherein the content of the amino alcohol is 0.1 to 5 wt % based on the total weight of the herbicidal emulsion composition.

8. The composition of claim 1, wherein the content of the polar nonaqueous solvent is 5 to 80 wt % based on the total weight of the herbicidal emulsion composition.

9. The composition of claim 1, wherein the ethenylamide compound is a compound selected from the group consisting of the following compounds:

2-chloro-N-(2-ethoxyethyl)-N-(2-methyl-1-phenyl-1-propenyl) acetamide, 2-chloro-N-(2-methoxyethyl)-N-(2-methyl-1-phenyl-1-propenyl) acetamide, 2-chloro-N-(2, 6-dimethyiphenyl)-N-(1-phenylethenyl) acetamide, 2-chloro-N-(2-ethoxyethyl)-N-(1-phenyl-1-propenyl) acetamide, N-(3-methoxypropyl)-N-(2-methyl-1-(4-methylphenyl)-1-propenyl) acetamide, 2-bromo-N-pentyl-N-(1-(3-chiorophenyl) ethenyl) acetamide, 2-methyl-N-(3-ethoxypropyl)-N-(2-methyl-1-(4-methoxyphenyl)-1-propenyl) propylamide, 2-chloro-N-phenyl-N-(2-methyl-1-4-methylthiophenyl-1-butenyl) acetamide, N-(3-propoxyproyl)-N-(2-methyl-1-(4-cyanophenyl)-1-propenyl) benzamide, 4-ethyl-N-(2-thienyl)-N-(1-(1-naphthyl)-1-butenyl) benzamide, 4-methoxy-N-ethyl-N-(2-methyl-1-(2-pyridyl)-1-propenyl) benzamide, 2-methxoy-N-butyl-N-(2-methyl-1-(2-thienyl)-1-propenyl) acetamide, 2-chloro-N-(2-4-methoxythienyl)-N-(2-methyl-1-(2-furyl)-1-propenyl) acetamide, 2-chloro-N-(2, 4-dichiorophenyl)-N-(1-phenylethenyl) acetamide, 2-bromo-N-methoxymethyl-N-(1-(2, 4-dimethyiphenyl)-1-propenyl) acetamide, 2-chloro-N-(2,6-dimethyiphenyl)-N-(1-(N-methylpyrimidinyl) ethenyl) acetamide, N-(1-naphthyl-N-(2-methyl-1-(4-bromophenyl)-1-propenyl) propylamide, 2,2,2-trifluoro-N-(2-methylthioethyl)-N-(1-(4-isopropylphenyl)-1-pentenyl) acetamide, N-(2-ethoxycarbonylethyl)-N-(1-(2-(4-methoxythionyl)) ethenylbenzamide and N-ethyl-N-(1-(4-nitrophenyl)-2-cyclohexylethenyl) thiazoamide.

10. The composition of claim 1, wherein the dichioroacetamide compound is a compound selected from the group consisting of the following compounds:

2,2,5-trimethyl-3-dichloroacetyloxazolidine, 2,2-dimethyl-3-dichioroacetyloxazolidine, 2-ethyl-2-methyl-3-dichioroacetyloxazolidine, 2,2-dimethyl-5-(2-furyl)-3-dichioroacetyloxazolidine, 2-methyl-5-(2-(4-methylfuryl) )-3-dichiorooxazolidine, 5-dichloroacetyl-3,3,6-trimethyl-9-oxo-1,5-diazabicyclo [4.3.0) nonane, 4-dichloroacetyl-5-methyl-9-oxo-1,4-diazabicyclo[3.4.0] nonane, 4-dichloroacetyl-9-oxo-1,5-diazabicyclo[3.4.0]nonane, 5-dichloroacetyl-6-ethyl-9-oxo-1,5-diazabicyclo[4.3.0] nonane, and 5-dichloroacetyl-3,3,6-trimethyl-10-oxo-1,5-azabicyclo [4.4.0]decane.

11. The composition of claim 1, wherein the amino alcohol is a compound selected from the group consiting of the following compounds: ethanolamine, 1-amino-2-propanol (isopropanolamine), 2-amino-1-propanol, 3-amino-1-propanol, 1-amino-2-butanol, 2-amino-1-butanol, 4-amino-1-butanol, 2-amino-2-methyl-1-propanol, diethanolamine, triethanolamine, diisopropanolamine and triisopropanolamine.

12. The composition of claim 1, wherein the polar nonaqueous solvent is a solvent selected from the group consisting of the following solvents: nitrogen-containing solvents, dimethyl sulfoxide, ketones, esters, and alcohols.

13. The composition according to claim 12, wherein the polar nonaqueous solvent is a solvent selected from the group consisting of the following solvents: N-methyl-2-pyrrolidone, N,N-dimethylformamide, dimethylsulfoxide, hexamethyiphosphoric acid triamide, acetone, methyl ethyl ketone, diisobutyl ketone, cyclohexanone, acetophenone, isophorone, ethyl acetate, arriyl acetate, ethylene glycol acetate, butyl maleate, diethyl succinate, methanol, n-hexanol, ethylene glycol, and diethylene glycol.

14. The composition according to claim 1, wherein the dichloroacetamide compound is used in an amount of 0.1 to 1 part by weight based on 1 part by weight of the ethenylamide compound.

15. The composition according to claim 1, wherein the dichloroacetamide compound is 3 to 45 wt % of the ethenylamide compound, dichloroacetamide compound, amino alcohol and polar nonaqueous solvent.

16. The composition according to claim 1, wherein the dichloroacetamide compound is 5 to 20 wt % of the ethenylamide compound, dichloroacetamide compound, amino alcohol and polar nonaqueous solvent.

17. The composition according to claim 1, wherein the composition further comprises a surfactant.

18. The composition according to claim 1, wherein the composition further comprises a nonpolar solvent.

19. The composition according to claim 17, wherein the surfactant is cationic, anionic, or amphoteric.

20. The composition according to claim 18, wherein the nonpolar solvent is benzene, toluene, xylene, ethylbenzene, coumene, methyl napthalene, kerosene, mineral oil, spindle oil, or white oil.

* * * * *